United States Patent
Heininger

Patent Number: 6,117,120
Date of Patent: Sep. 12, 2000

[54] URINARY CATHETER SYSTEM

[76] Inventor: Elise Heininger, 26130 93rd St., Salem, Wis. 53168-9327

[21] Appl. No.: 09/307,349

[22] Filed: May 6, 1999

[51] Int. Cl.$^7$ ........................................................ A61F 5/44
[52] U.S. Cl. ............................................ 604/349; 604/347
[58] Field of Search ..................................... 604/346, 544, 604/347, 349, 350, 351, 327–336, 352

[56] References Cited

U.S. PATENT DOCUMENTS

| | | | |
|---|---|---|---|
| 4,387,726 | 6/1983 | Denard .................................... | 128/760 |
| 5,695,485 | 12/1997 | Duperret et al. ........................ | 604/349 |
| 5,752,944 | 5/1998 | Dann et al. .............................. | 604/352 |

*Primary Examiner*—Corrine McDermott
*Assistant Examiner*—Ann Y. Lam

[57] ABSTRACT

A catheter system for providing a secure fit over a user's penis. The catheter system includes a tubular outer sheath has proximal and distal ends. A collection bag is in fluid communication with the distal end of the outer sheath. A tubular elastic inner sheath is disposed in the outer sheath. The inner sheath has open proximal and distal ends. A tubular insert has open proximal and distal ends and is disposed in the inner sheath. The proximal and distal ends of the insert each has an inwardly radiating elastic annular membrane. An annular collar is provide having a water absorbent inwardly radiating annular membrane. The annular collar is coupled to the proximal end of the outer sheath.

5 Claims, 2 Drawing Sheets

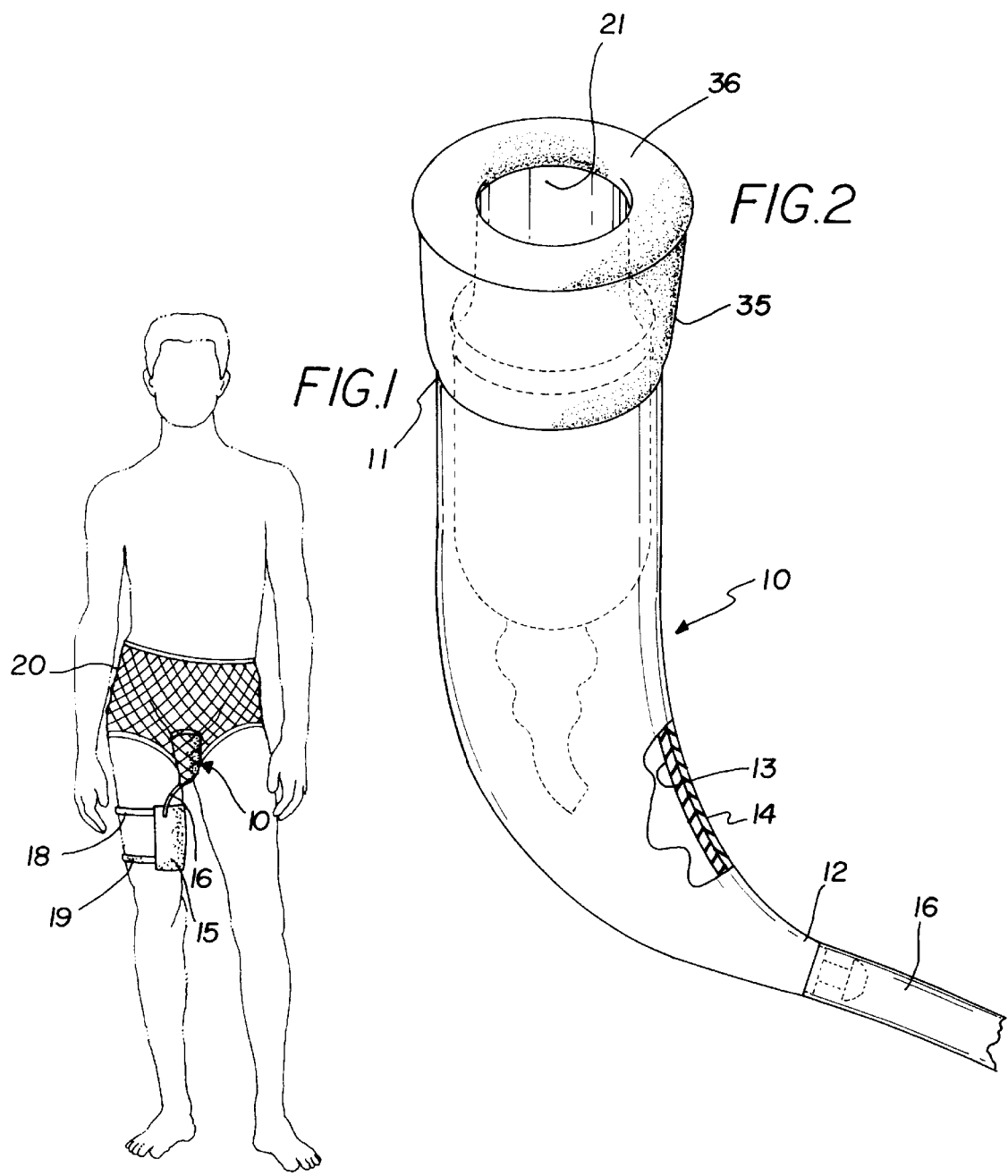

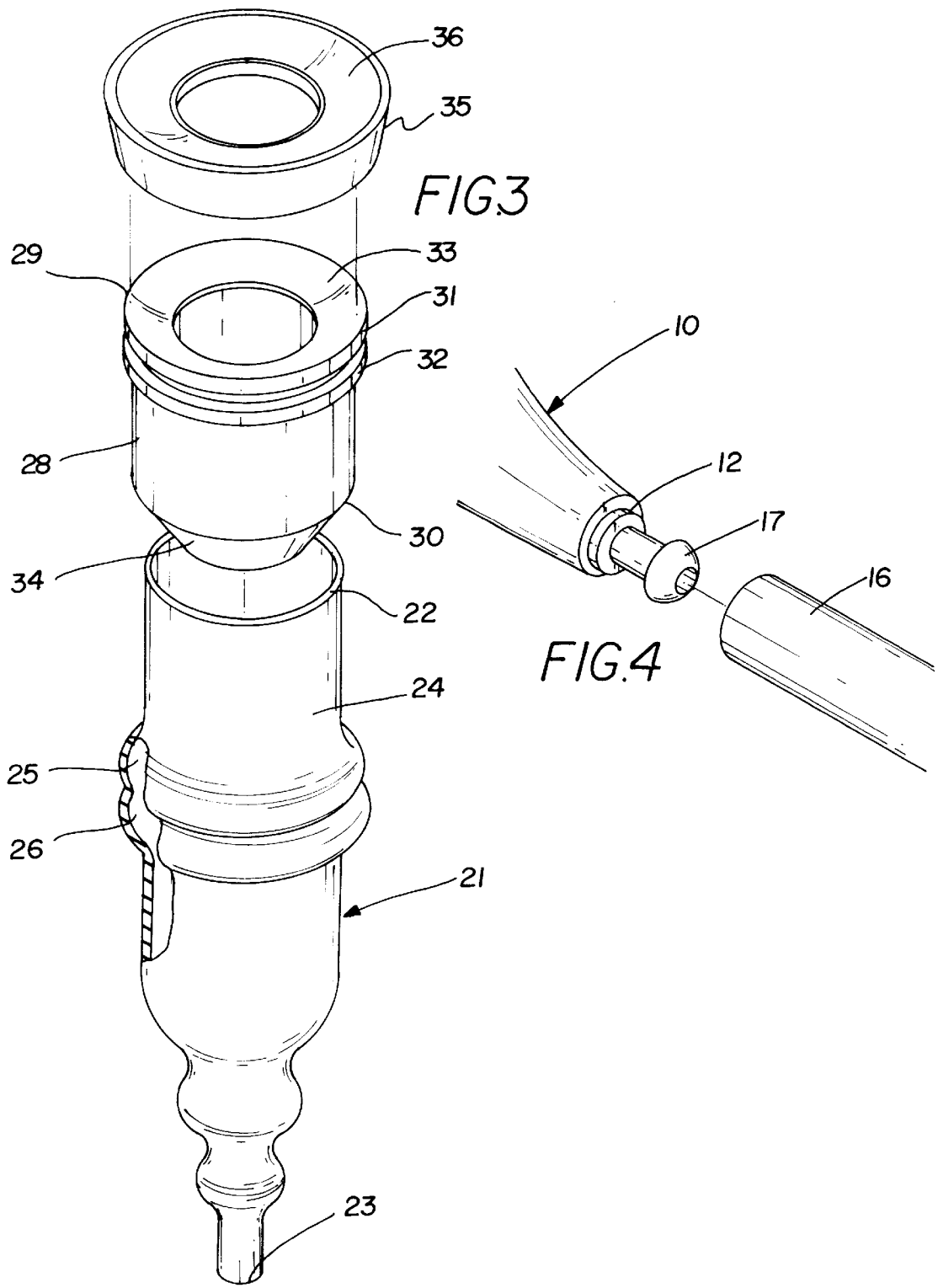

URINARY CATHETER SYSTEM

BACKGROUND OF THE INVENTION

1. Field of the Invention

The present invention relates to urinary catheters and more particularly pertains to a new catheter system for providing a secure fit over a user's penis.

2. Description of the Prior Art

The use of urinary catheters is known in the prior art. More specifically, urinary catheters heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,713,880; U.S. Pat. No. 4,020,843; U.S. Pat. No. 4,568,340; U.S. Pat. No. 2,940,450; U.S. Pat. No. 1,372,101; and U.S. Pat. No. Des. 299,865.

While these devices fulfill their respective, particular objectives and requirements, the aforementioned patents do not disclose a new catheter system. The inventive device includes a tubular outer sheath has proximal and distal ends. A collection bag is in fluid communication with the distal end of the outer sheath. A tubular elastic inner sheath is disposed in the outer sheath. The inner sheath has open proximal and distal ends. A tubular insert has open proximal and distal ends and is disposed in the inner sheath. The proximal and distal ends of the insert each has an inwardly radiating elastic annular membrane. An annular collar is provide having a water absorbent inwardly radiating annular membrane. The annular collar is coupled to the proximal end of the outer sheath.

In these respects, the catheter system according to the present invention substantially departs from the conventional concepts and designs of the prior art, and in so doing provides an apparatus primarily developed for the purpose of providing a secure fit over a user's penis.

SUMMARY OF THE INVENTION

In view of the foregoing disadvantages inherent in the known types of urinary catheters now present in the prior art, the present invention provides a new catheter system construction wherein the same can be utilized for providing a secure fit over a user's penis.

The general purpose of the present invention, which will be described subsequently in greater detail, is to provide a new catheter system apparatus and method which has many of the advantages of the urinary catheters mentioned heretofore and many novel features that result in a new catheter system which is not anticipated, rendered obvious, suggested, or even implied by any of the prior art urinary catheters, either alone or in any combination thereof.

To attain this, the present invention generally comprises a tubular outer sheath has proximal and distal ends. A collection bag is in fluid communication with the distal end of the outer sheath. A tubular elastic inner sheath is disposed in the outer sheath. The inner sheath has open proximal and distal ends. A tubular insert has open proximal and distal ends and is disposed in the inner sheath. The proximal and distal ends of the insert each has an inwardly radiating elastic annular membrane. An annular collar is provide having a water absorbent inwardly radiating annular membrane. The annular collar is coupled to the proximal end of the outer sheath.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new catheter system apparatus and method which has many of the advantages of the urinary catheters mentioned heretofore and many novel features that result in a new catheter system which is not anticipated, rendered obvious, suggested, or even implied by any of the prior art urinary catheters, either alone or in any combination thereof.

It is another object of the present invention to provide a new catheter system which may be easily and efficiently manufactured and marketed.

It is a further object of the present invention to provide a new catheter system which is of a durable and reliable construction.

An even further object of the present invention is to provide a new catheter system which is susceptible of a low cost of manufacture with regard to both materials and labor, and which accordingly is then susceptible of low prices of sale to the consuming public, thereby making such catheter system economically available to the buying public.

Still yet another object of the present invention is to provide a new catheter system which provides in the apparatuses and methods of the prior art some of the advantages thereof, while simultaneously overcoming some of the disadvantages normally associated therewith.

Still another object of the present invention is to provide a new catheter system for providing a secure fit over a user's penis.

Yet another object of the present invention is to provide a new catheter system which includes a tubular outer sheath has proximal and distal ends. A collection bag is in fluid communication with the distal end of the outer sheath. A tubular elastic inner sheath is disposed in the outer sheath.

The inner sheath has open proximal and distal ends. A tubular insert has open proximal and distal ends and is disposed in the inner sheath. The proximal and distal ends of the insert each has an inwardly radiating elastic annular membrane. An annular collar is provide having a water absorbent inwardly radiating annular membrane. The annular collar is coupled to the proximal end of the outer sheath.

Still yet another object of the present invention is to provide a new catheter system that comfortably holds a catheter in place on a user's penis. This catheter system is worn on and around the penis and does not have any parts that are inserted into the urethra and thereby makes this catheter system even more comfortable for a user to wear.

Even still another object of the present invention is to provide a new catheter system that blocks fluids and moisture from leaking out around the user's penis.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic front view of a new catheter system in use according to the present invention.

FIG. 2 is a schematic perspective view of the present invention.

FIG. 3 is a schematic exploded perspective view of the present invention.

FIG. 4 is a schematic enlarged exploded perspective view of the connection between the flexible tube and the distal end of the outer sheath.

DESCRIPTION OF THE PREFERRED EMBODIMENT

With reference now to the drawings, and in particular to FIGS. 1 through 4 thereof, a new catheter system embodying the principles and concepts of the present invention will be described.

As best illustrated in FIGS. 1 through 4, the catheter system generally comprises a tubular outer sheath has proximal and distal ends. A collection bag is in fluid communication with the distal end of the outer sheath. A tubular elastic inner sheath is disposed in the outer sheath. The inner sheath has open proximal and distal ends. A tubular insert has open proximal and distal ends and is disposed in the inner sheath. The proximal and distal ends of the insert each has an inwardly radiating elastic annular membrane. An annular collar is provide having a water absorbent inwardly radiating annular membrane. The annular collar is coupled to the proximal end of the outer sheath.

In closer detail, the urinary catheter system comprises a tubular outer sheath 10 having open proximal and distal ends 11,12. The outer sheath preferably tapers in diameter towards the distal end of the outer sheath. The outer sheath preferably comprises a non-kinking rigid plastic inner layer 13 surrounded by a soft latex outer layer 14. The proximal end of the outer sheath has a generally circular opening therein designed for inserting therein a user's penis.

A collection bag 15 is provided for holding a fluid such as urine therein. An elongate flexible tube 16 fluidly connects the distal end of the outer sheath to the collection bag. The distal end of the outer sheath has a mushroom shaped tube connector 17 around the opening of the distal end which is inserted into one end of the flexible tube to couple the distal end of the outer sheath to the flexible tube. Preferably, the collection bag has a pair of straps 18,19 designed for securing the collection bag to a user's leg. A net mesh undergarment 20 may be provided for wear by a user. The undergarment has a plurality of holes therethrough formed by the net mesh. The outer sheath is held in the undergarment when worn by a user such that the flexible tube extends out through one of the holes of the undergarment. Optionally, a hole in the front of the undergarment may be enlarged to permit extension of a distal portion of the outer tube to extent out of the undergarment as well.

A tubular elastic and flexible inner sheath 21 is disposed in the outer sheath. The inner sheath comprising an elastic latex material. The inner sheath has generally circular open proximal and distal ends 22,23, and a lumen. The inner sheath tapers towards the distal end of the inner sheath so that the proximal end of the inner sheath has greater outer diameter than the distal end of the inner sheath. The proximal end of the inner sheath is outwardly extended from the proximal end of the outer sheath. The distal end of the inner sheath is positioned in the outer sheath between the proximal and distal ends of the outer sheath.

Preferably, the inner sheath has a generally cylindrical proximal portion 24 adjacent the proximal end of the inner sheath designed for receiving a user's penis therein. The proximal portion of the inner sheath has a pair of outwardly radiating annular retaining grooves 25,26 in the lumen of the inner sheath. The retainer grooves of the inner sheath also define corresponding outwardly radiating annular ridges extending from the inner sheath which abut an inner surface of the outer sheath to frictionally hold the inner sheath in a fixed position in the outer sheath. The inner sheath also preferably has a plurality of annular constrictions 27 located towards the distal end of the inner sheath, the annular constrictions of the inner sheath defining therebetween a plurality of bulbous portions of the inner sheath.

A generally cylindrical tubular insert 28 is provided having open proximal and distal ends 29,30. The insert comprises a rigid plastic material. The insert has a pair of retaining ridges 31,32 outwardly radiating therefrom adjacent the proximal end of the insert. The insert is disposed in the proximal portion of the inner sheath such that the insert is positioned between the proximal and distal ends of the inner sheath. The proximal end of the insert is orientated towards the proximal end of the inner sheath and the distal end of the insert is orientated towards the distal end of the inner sheath. The retaining ridges is inserted into the retaining grooves to hold the insert in a fixed position in the inner sheath.

The proximal and distal ends of the insert each have an inwardly radiating generally frusta-conical elastic annular membrane 33,34. The elastic membranes each have an inner periphery extending towards the distal end of the inner sheath. The insert is designed for extending therethrough a user's penis inserted into the inner sheath. The elastic membranes are designed for disposing around the user's penis such that the user's penis stretches the elastic collars such that the elastic membranes hold the insert on the user's penis.

An annular collar 35 is provided having a water absorbent inwardly radiating annular membrane 36 such as a chamois material. The annular collar is coupled by friction fitting to the proximal end of the outer sheath such that the proximal end of the inner sheath is positioned in the annular collar. The annular collar is designed for extending a user's penis therethrough to permit insertion of the penis into the inner sheath and insert. The water absorbent annular membrane of the annular collar is designed positioning around the user's penis for absorbing any water based fluids that may leak out from the proximal end of the outer sheath.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A urinary catheter system, comprising:
   a tubular outer sheath having proximal and distal ends;
   a collection bag in fluid communication with said distal end of said outer sheath;
   a tubular elastic inner sheath being disposed in said outer sheath;
   said inner sheath having open proximal and distal ends, and a lumen;
   a tubular insert having open proximal and distal ends and being disposed in said inner sheath;
   said proximal and distal ends of said insert each having an inwardly radiating elastic annular membrane; and
   an annular collar having a water absorbent inwardly radiating annular membrane, said annular collar being coupled to said proximal end of said outer sheath.

2. The urinary catheter system of claim 1, wherein said outer sheath tapers towards said distal end of said outer sheath.

3. The urinary catheter system of claim 1, wherein an elongate flexible tube fluidly connects said distal end of said outer sheath to said collection bag.

4. The urinary catheter system of claim 1, wherein said inner sheath has a pair of outwardly radiating annular retaining grooves in said lumen of said inner sheath, wherein said insert has a pair of retaining ridges outwardly radiating therefrom adjacent said proximal end of said insert, wherein said retaining ridges are inserted into said retaining grooves to hold said insert in a fixed position in said inner sheath.

5. A urinary catheter system, comprising:
   a tubular outer sheath having proximal and distal ends, said outer sheath tapering towards said distal end of said outer sheath;
   said proximal end of said outer sheath having a generally circular opening therein adapted for inserting therein a user's penis;
   a collection bag for holding a fluid therein, said collection bag having a pair of straps adapted for securing said collection bag to a user's leg;
   an elongate flexible tube fluidly connecting said distal end of said outer sheath to said collection bag;
   a tubular flexible inner sheath being disposed in said outer sheath;
   said inner sheath having open proximal and distal ends, and a lumen;
   said proximal end of said inner sheath being outwardly extended from said proximal end of said outer sheath;
   said distal end of said inner sheath being positioned in said outer sheath between said proximal and distal ends of said outer sheath;
   said inner sheath having a generally cylindrical proximal portion adjacent said proximal end of said inner sheath adapted for receiving a user's penis therein;
   said proximal portion of said inner sheath having a pair of outwardly radiating annular retaining grooves in said lumen of said inner sheath;
   a generally cylindrical insert having open proximal and distal ends, said insert comprising a rigid material;
   said insert having a pair of retaining ridges outwardly radiating therefrom adjacent said proximal end of said insert;
   said insert being disposed in said proximal portion of said inner sheath;
   said proximal end of said insert being orientated towards said proximal end of said inner sheath and said distal end of said insert being orientated towards said distal end of said inner sheath;
   said retaining ridges being inserted into said retaining grooves to hold said insert in a fixed position in said inner sheath;
   said proximal and distal ends of said insert each having an inwardly radiating generally frusta-conical elastic annular membrane;
   said insert being adapted for extending therethrough a user's penis inserted into said inner sheath, said elastic membranes being adapted for disposing around the user's penis such that the user's penis stretches said elastic collars such that said elastic membranes hold said insert on the user's penis; and
   an annular collar having a water absorbent inwardly radiating annular membrane, said annular collar being coupled to said proximal end of said outer sheath such that said proximal end of said inner sheath is positioned in said annular collar, said annular collar being adapted for extending a user's penis therethrough to permit insertion of the penis into the inner sheath and insert.

* * * * *